(12) United States Patent
Mashima et al.

(10) Patent No.: US 7,977,271 B2
(45) Date of Patent: Jul. 12, 2011

(54) MULTIPLE-METAL COMPLEX-CONTAINING COMPOUND AND METAL COMPLEX, AND MANUFACTURE METHODS THEREFOR, AND EXHAUST GAS PURIFICATION CATALYST MANUFACTURE METHOD USING THE SAME

(75) Inventors: Kazushi Mashima, Ikeda (JP); Masato Ohashi, Minoo (JP); Akihiro Yagyu, Koube (JP); Hirohito Hirata, Suntou-gun (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 162 days.

(21) Appl. No.: 12/281,186

(22) PCT Filed: Feb. 28, 2007

(86) PCT No.: PCT/IB2007/000533
§ 371 (c)(1), (2), (4) Date: Dec. 16, 2008

(87) PCT Pub. No.: WO2007/105052
PCT Pub. Date: Sep. 20, 2007

(65) Prior Publication Data
US 2010/0152029 A1 Jun. 17, 2010

(30) Foreign Application Priority Data
Mar. 1, 2006 (JP) .................................. 2006-055607

(51) Int. Cl.
 B01J 31/12 (2006.01)
 B01J 31/20 (2006.01)
 B01J 37/08 (2006.01)
 B01J 37/02 (2006.01)
 C07F 15/00 (2006.01)
(52) U.S. Cl. .................. 502/170; 556/136; 502/161
(58) Field of Classification Search .................. None
See application file for complete search history.

(56) References Cited

U.S. PATENT DOCUMENTS

| | | |
|---|---|---|
| 3,367,888 A | 2/1968 | Hoekstra |
| 3,388,077 A | 6/1968 | Hoekstra |
| 3,998,759 A | 12/1976 | Hoekstra |

(Continued)

FOREIGN PATENT DOCUMENTS

DE   3727704 A1   3/1989

(Continued)

OTHER PUBLICATIONS

Jain et al.: *The chemistry of binuclear palladium(II) and platinum(II) complexes*, Coordination Chemistry Reviews, Elsevier Science, Amsterdam, NL, vol. 249, No. 24, Sep. 15, 2005 pp. 3075-3197.

(Continued)

*Primary Examiner* — Melvin C Mayes
*Assistant Examiner* — Yun Qian
(74) *Attorney, Agent, or Firm* — Kenyon & Kenyon LLP (57) ABSTRACT

A multiple-metal complex-containing compound in accordance with an embodiment has a plurality of metal complexes in each of which a ligand is coordinated to one metal atom or a plurality of metal atoms of the same kind. The plurality of metal complexes are bound to each other via a polydentate ligand that substitutes partially the ligands of the two or more metal complexes, and have 2 to 1000 metal atoms.

2 Claims, 8 Drawing Sheets

U.S. PATENT DOCUMENTS

| | | | |
|---|---|---|---|
| 5,017,541 | A | 5/1991 | Schmidt |
| 5,643,508 | A | 7/1997 | Ganguly |

FOREIGN PATENT DOCUMENTS

| | | | |
|---|---|---|---|
| EP | 0864362 | A1 | 9/1998 |
| EP | 0934774 | A2 | 8/1999 |
| EP | 1712277 | A | 10/2006 |
| EP | 1886726 | A1 | 2/2008 |
| GB | 1035983 | A | 7/1966 |
| JP | 64-070596 | A | 3/1989 |
| JP | 09253490 | A | 9/1997 |
| JP | 10-251548 | A | 9/1998 |
| JP | 11285644 | A | 10/1999 |
| JP | 2000-109485 | * | 4/2000 |
| JP | 2000/109485 | A | 4/2000 |
| JP | 2003/181288 | A | 7/2003 |
| JP | 2005-270883 | A | 10/2005 |
| WO | 2005/092493 | A | 10/2005 |
| WO | 2006/121205 | A1 | 11/2006 |
| WO | 2007/099449 | A2 | 9/2007 |
| WO | 2007/141662 | A2 | 12/2007 |

OTHER PUBLICATIONS

Shibata A., et al: *Synthesis and property of pentakis(mu-acetato-0,0')(linear-hexamine)tetraplatinum(II), [Pt$_4$($\mu$-acetato0, 0')$_5$ (L)]$^{3+}$; correlation between rate of in-plane acetate ligand exchange and catalytic activity for hydration of acetonitrile*, Inorganica Chimica ACTA, Elsevier BV, NL, vol. 265, No. 1-2 Part II, Jan. 1, 1997, pp. 197-204.

Asakura, Kiyotaki et al "In-Situ Polarization-Dependent Total-Reflection Fluorescence XAFS Studies on the Structure Transformation of Pt Clusters on .alpha.-A1203(0001)", Journal of Physical Chemistry B, 1997, pp. 5549-5556, (101), ACS Publications, Washington, DC, USA.

Chun, Wang-Jae et al "Surface structure change of a [Pt4(.mu.-CH3C00)8]/Si02 catalyst active for the decomposition of formic acid", Journal of the Chemistry Society, Faraday Transactions, 1995, pp. 4161-4170, 91(22), RSC Publishing, Piccadilly, London, UK.

Iwasawa, Y "Chemical design and characterization of catalysts and catalysis: an approach to dynamic catalyst design", Catalysis Today, 1993, pp. 21-72,18(1), Elsevier Science Publishers B.V., Amsterdam, NL.

Judai, Ken et al "Low-Temperature Cluster Catalysis", Journal of the American Chemical Society, 2004, pp. 2732-2737, 126(9), ACS Publications, Washington, DC, USA.

Argo, A M et al "Observation of ligand effects during alkene hydrogenation catalysed by supported metal clusters", Nature, Feb. 7, 2002, pp. 623-626, (415), Macmillan Magazines Ltd, New York, NY, USA.

Oosterom, G Eric et al "Transition Metal Catalysis Using Functionalized Dendrimers", Angewandte Chemie International Edition, May 18, 2001, pp. 1829-1849, 40(10), Wiley-VCH Verlag, Weinheim, DE.

Lang, Huilang et al "Dendrimer-Encapsulated Nanoparticle Precursors to Supported Platinum Catalysts", Journal of the American Chemical Society, Nov. 7, 2003, pp. 14832-14836, 125(48), ACS Publications, Washington, DC, USA.

Mecking, Stefan et al "Preparation of Catalytically Active Palladium NanoClusters in Compartments of Amphiphilic Hyperbranched Polyglycerols", Macromolecules, May 9, 2000, pp. 3958-3960, 33(11), ACS Publications, Washington, DC, USA.

Liebscher, W et al "Nomenklatur der Anorganischen Chemie", International Union of Pure and Applied Chemistry—Deutsche Ausgabe der Empfehlungen 1990, 1994, pp. 177-251, VCH Verlagsgesellschaft mbH, Weinheim, DE.

Cotton, F Albert et al "Supramolecular Arrays Based on Dimetal Building Units", Accounts of Chemical Research, Aug. 17, 2001, pp. 759-771, 34(10), ACS Publications, Washington, DC, USA.

Chisholm, Malcolm H "Compounds in which the Mo24+ unit is embraced by one, two or three formamidinate ligands together with acetonitrile ligands", Journal of the Chemical Society, Dalton Transactions, 1999, pp. 1387-1391, 1999(9), RSC Publishing, Piccadilly, London, UK.

Cotton, F Albert et al "Trishomobarrelenedicarboxylate dianion as a bridge between dimolybdenum units: Comparison to similar compounds", Polyhedron, Aug. 11, 2005, pp. 219-223, 25(2), Elsevier Science Publishers B. V., Amsterdam, NL.

Cotton, F Albert et al "Polyunsaturated Dicarboxylate Tethers Connecting Dimolybdenum Redox and Chromophoric Centers: Syntheses, Structures, and Electrochemistry", Journal of the American Chemical Society, 2003, pp. 5436-5450, 125(18), ACS Publications, Washington, DC, USA.

Cotton, F Albert et al "The first supramolecular assemblies comprised of dimetal units and chiral dicarboxylates", Inorganic Chemistry Communications, 2002, pp. 59-63, 5(1), Elsevier Science Publishers B.V., Amsterdam, NL.

Chisholm, Malcolm H et al "Electronically Coupled MM Quadruply-Bonded Complexes (M=Mo or W) Employing Functionalized Terephthalate Bridges: Toward Molecular Rheostats and Switches", Journal of the American Chemical Society, 2005, pp. 18150-18158, 127(51), ACS Publications, Washington, DC, USA.

Barybin, Mikhail V et al "Long-Range Electronic Coupling of MM Quadruple Bonds (M=Mo or W) via a 2,6-Azulenedicarboxylate Bridge", Journal of the American Chemical Society, 2005, pp. 15182-15190, 127(43), ACS Publications, Washington, DC, USA.

Byrnes, Matthew J et al "Thienyl Carboxylate Ligands Bound to and Bridging MM Quadruple Bonds, M=Mo or W: Models for Polythiophenes Incorporating MM Quadruple Bonds", Inorganic Chemistry, 2004, pp. 6334-6344, 43 (20), ACS Publications, Washington, DC, USA.

Byrnes, Matthew J et al "9,10-Anthracene dicarboxylate bridged complexes with M2 quadruply bonded dimetal units: [{M2(02CtBu)3}2(.mu.-9,10-An(CO2)2)], where M=Mo or W", Journal of the Chemistry Society, Dalton Transactions, 2004, pp. 523-529, (4), RSC Publishing, Piccadilly, London, UK.

Cayton, Roger H et al "Metal-metal multiple bonds in ordered assemblies. 1. Tetranuclear molybdenum and tungsten carboxylates involving covalently linked metal-metal quadruple bonds. Molecular models for subunits of one-dimensional stiff-chain polymers", Journal of the American Chemical Society, 1991, pp. 8709-8724, 113(23), ACS Publications, Washington, DC, USA.

Canadell, E. et al "Possibility of synthesizing dinolybdenum acetate derivative polymers: theoretical point of view and experimental attempts", New Journal of Chemistry, 1991, pp. 623-628, 15(8-9), RSC Publishing, Piccadilly, London, UK.

Bonar-Law, Richard P. et al "Dirhodium(II) carboxylates as building blocks. Macrocyclic dimers with vertically stacked Rh24+ units", Journal of the Chemistry Society, Dalton Transactions, 2000, pp. 4244-4246, (23), RSC Publishing, Piccadilly, London, UK.

Leininger, Stefan et al "Self-Assembly of Discrete Cyclic Nanostructures Mediated by Transition Metals", Chemical Reviews, 2000, pp. 853-907, 100(3), ACS Publications, Washington, DC, USA.

Oldham, Colin et al "Metal complexes of Group 1B. Part 1. Triphenylphosphinesilver (I) carboxylates", Journal of the Chemical Society, Dalton Transactions, 1977, pp. 2068-2070, (20), RSC Publishing, Piccadilly, London, UK.

Eshaque, M et al "D-Mannitol platinum complexes", Journal of Clinical Hematology and Oncology, 1977, pp. 338-348, 7(1), Wadley Institutes of Molecular Medicine, Dallas, TX, USA.

Darensbourg, Donald J et al "Structural characterizations of coordination complexes of bis-triphenylphosphine copper (I) dicarboxylates", Polyhedron, 1996, pp. 2341-2349, 15(14), Elsevier Science Publishers B.V., Amsterdam, NL.

Ogino, Hiroshi et al "Stoichiometric, kinetic, and mechanistic investigations of the reactions of (oxygen-bonded aminopolycarboxylato)pentaamminecobalt(III) complexes with hexaaquachromium(II) ions", Inorganic Chemistry, 1991, pp. 255-259, 19(1), ACS Publications, Washington, DC, USA.

Ogino, Hiroshi et al "Syntheses and characterizations of .mu.-dicarboxylatobis [pentaamminecobalt(III)] complexes", Bulletin of the Chemical Society of Japan, 1981, pp. 1746-1749, 54(6), CSJ Publications, Tokyo, JP.

Kansikas, Jarno "X-ray structural studies of six complexes formed by N1-isopropyl-2-methyl-1,2-propanediamine with copper(II)

dicarboxylates", Annales Academiæ Scientiarum Fennicæ, Series A2: Chemicæ, 1985, p. 69, (206) Helsinki, FL.

Burrows, Andrew D. et al "Platinum(II) phosphine complexes of dicarboxylates and ammonia: crystal structures of [{Pt(PPh3)2(NH3)2}2{.mu.-1,3-(02C)2C6H4}2], [{Pt(PPh3)2(NH3)}2{.mu.-1,4-(02C)2C6H4}][PF6]2 and cis-[Pt(PPh3)2(NH3)2][NO3]2", Journal of the Chemical Society, Dalton Transactions: Inorganic Chemistry, 1997, pp. 1295-1300, (8), RSC Publishing, Piccadilly, London, UK.

Massoud, Salah S. et al "Dinuclear terephthalato-bridged copper(II) complexes: Syntheses, spectral and structural characterization, and magnetic properties", Inorganica Chimica Acta, 2006, pp. 1489-1500, 359(5), Elsevier Science Publishers B.V., Amsterdam, NL.

Bobtelsky, M et al "The Structure and Behavior of Ferric Tartrate and Citrate Complexes in Dilute Solutions", Journal of the American Chemical Society, 1947, pp. 2286-2290, 69, ACS Publications, Washington, DC, USA.

Ershov, B G "The nature of colloidal platinum in aqueous solution: features of catalytic reactions", Russian Chemical Bulletin, International Edition, 2001, pp. 626-630, 50(4), Springer, New York, NY, USA.

Yu, Yong et al "Syntheses, Structures, and Reactivity of Radial Oligocyclopentadienyl Metal Complexes: Penta (ferrocenyl)cyclopentadienyl and Congeners", Angewandte Chemie, 2006, pp. 1823-1381, 118(11), Wiley-VCH Verlag, Weinheim, DE.

Crooks, Richard M et al "Dedrimer-Encapsulated Metal Nanoparticles: Synthesis, Characterization, and Applications to Catalysis", Accounts of Chemical Research, 2000, pp. 181-190, 34(3), ACS Publications, Washington, DC, USA.

Grubbs, Robert H (Ed.) "Handbook of Metathesis", 2003, pp. 403-431, 2, Wiley-VCH Verlag, Weinheim, DE.

Ruwwe, J et al "Olefin Metatheses in Metal Coordination Spheres: Versatile New Strategies for the Construction of Novel Monohapto or Polyhapto Cyclic, Macrocyclic, Polymacrocyclic, and Bridging Ligands", Chemistry—A European Journal, 2001, 7(18), Wiley-VCH Verlag, Weinheim, DE.

Grubbs, Robert H "Olefin Metathesis", Tetrahedron, 2007, pp. 7117-7140, 60(34), Elsevier Science Publishers B. V., Amsterdam, NL.

Trnka, Tina M et al "The Development of L2X2RU=CHR Olefin Metathesis Catalysts: An Organometallic Success Story", Accounts of Chemical Research, 2001, pp. 18-29, 34(1), ACS Publications, Washington, DC, USA.

Ohashi, Masato et al "Metathesis Approach to Linkage of Two Tetraplatinum Cluster Units: Synthesis, Characterization, and Dimerization of [Pt4(μ-OCOCH3)7(μ-OCO(CH2)nCH=CH2)] (n=0-3)" Chemistry Letters, 2006, pp. 954-955, 35(8), CSJ Publications, Tokyo, JP.

Chen, Wei-Zhong et al "Dimerization of Diruthenium Coordination Compounds via Olefin Metathesis", European Journal of Inorganic Chemistry, 2006, pp. 4737-4740, (23), Wiley-VCH Verlag, Weinheim, DE.

Chen, Wei-Zhong et al "Olefin Metathesis as an Inorganic Synthetic Tool: Cross and Ring Closing Metathesis Reactions of Diruthenium-Bound .omega.-Alkene-.alpha.-carboxylates", Inorganic Chemistry, 2007, pp. 3775-3782, 46(9), ACS Publications, Washington, DC, USA.

Ichihashi, Masahiko et al Adsorption and Reaction of Methanol Molecule on Nickel Cluster Ions, NIn +(n=3-11), Journal of Physical Chemistry A, 2000, pp. 11885-11890, 104(51), ACS Publications, Washington, DC, USA.

"[octa-.mu.-acetato-tetraplatinum(II)] [Pt4(.mu.-CH3COO)8]=1252.68", The Fourth Series of Experimental Chemistry, 1991, p. 452, 17, The Chemical Society of Japan, Maruzen, Tokyo, JP.

* cited by examiner

[Pt₄(CH₃COO)₈]

+ CH₂=CH(CH₂)₃COOH

[Pt₄(CH₃COO)₇(O₂C(CH₂)₃CH=CH₂)]

FIG. 6

2 [Pt$_4$(CH$_3$COO)$_7$ {CH$_2$=CH(CH$_2$)$_3$COO}]

[Pt$_4$(CH$_3$COO)$_7$ [O$_2$C(CH$_2$)$_3$CH=CH(CH$_2$)$_3$CO$_2$] (CH$_3$COO)$_7$Pt$_4$]

R : (CH$_2$)$_3$CH=CH(CH$_2$)$_3$

GRUBBS CATALYST →

Page 1 / 2

MULTIPLE-METAL COMPLEX-CONTAINING COMPOUND AND METAL COMPLEX, AND MANUFACTURE METHODS THEREFOR, AND EXHAUST GAS PURIFICATION CATALYST MANUFACTURE METHOD USING THE SAME

This is a 371 national phase application of PCT/IB2007/000533 filed 28 Feb. 2007, claiming priority to Japanese Patent Application No. 2006-055607 filed 01 Mar. 2006, the contents of which are incorporated herein by reference.

BACKGROUND OF THE INVENTION

1. Field of the Invention

The invention relates to a multiple-metal complex-containing compound and a metal complex, and manufacture method therefor as well as an exhaust gas purification catalyst manufacture method using the same. In particular, the invention relates to a method of manufacturing a metal particle having a controlled cluster size through the use of the multiple-metal complex-containing compound and the metal complex.

2. Description of the Related Art

A size-controlled metal cluster is different from a bulk metal in chemical characteristics, such as catalytic activity and the like, and physical characteristics, such as magnetism and the like.

In order to efficiently utilize the peculiar characteristics of the metal cluster, a method for easily synthesizing a size-controlled cluster in large amount is needed. A known method for obtaining such a cluster is a method in which (i) clusters of various sizes are produced by causing a metal target to evaporate in vacuum, and (ii) the thus-obtained clusters are separated according to cluster sizes through the use of the principle of the mass spectrum. However, this method is not able to easily synthesize a cluster in large amount.

Figure 1:
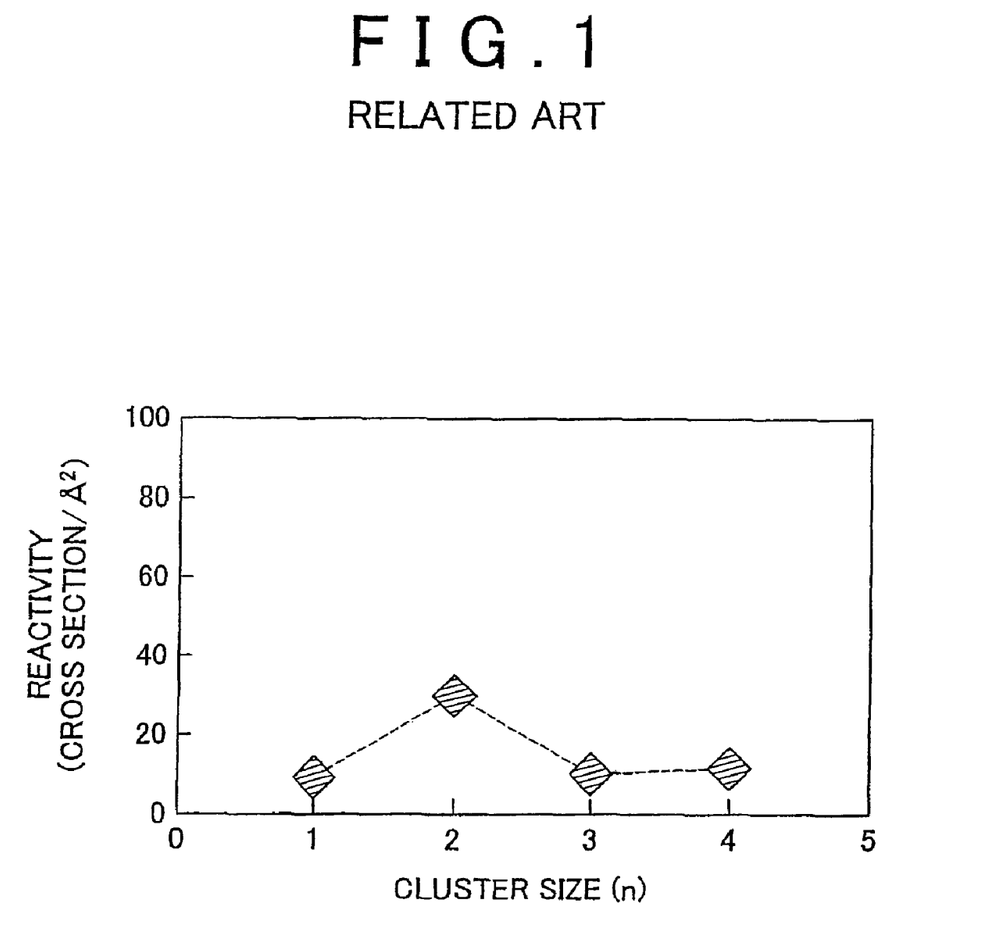
FIG. 1 is a graph showing a relationship between the Pt cluster size and the reactivity extracted from the aforementioned non-patent document.

The peculiar characteristics of the cluster is disclosed in, for example, "Adsorption and Reaction of Methanol Molecule on Nickel Cluster Ions, $Ni_n^+$ (n=3-11)", M. Ichihashi, T. Hanmura, R. T. Yadav and T. Kondow, J. Phys. Chem. A, 104, 11885 (2000) (non-patent document). This document discloses that the reactivity between methane molecules and platinum catalyst in the gas phase is greatly affected by the platinum cluster size, and that there exists a particular platinum cluster size that is optimal for the reaction, for example, as shown in FIG. 1.

Examples of utilization of the catalytic performance of a noble metal include purification of exhaust gas discharged from an internal combustin engine, such as an automotive engine or the like. At the time of the purification of exhaust gas, exhaust gas components, such as carbon monoxide (CO), hydrocarbon (HC), nitrogen oxide ($NO_x$), etc., are converted into carbon dioxide, nitrogen and oxygen by catalyst components whose main component is a noble metal such as platinum (Pt), rhodium (Rh), palladium (Pd), iridium (Ir), etc. Generally, the catalyst component that is a noble metal is supported on a support made of an oxide, such as alumina or the like, in order to enlarge the contact area for exhaust gas and the catalyst component.

In order to support a noble metal on the oxide support, the oxide support is impregnated with a solution of a nitric acid salt of a noble metal or a noble metal complex having one noble metal atom so that the noble metal compound is dispersed on surfaces of the oxide support, and then the support impregnated with the solution is dried and fired. In this method, however, it is not easy to control the size and the number of atoms of the noble metal cluster.

With regard to such catalysts for exhaust gas purification, too, the supporting of a noble metal in the form of clusters has been proposed in order to further improve the exhaust gas purification capability. For example, Japanese Patent Application Publication No. JP-A-11-285644 discloses a technology in which a catalytic metal is supported in the form of ultrafine particle directly on a support through the use of a metal cluster complex that has a carbonyl group as a ligand.

Furthermore, Japanese Patent Application Publication No. JP-A-2003-481288 discloses a technology in which a noble metal catalyst having a controlled cluster size is manufactured by introducing a noble metal into pores of a hollow carbon material, such as carbon nanotube or the like, and fixing the carbon material with the noble metal introduced therein to an oxide support, and then firing it.

Still further, Japanese Patent Application Publication No. JP-A-9-253490 discloses a technology in which a metal cluster made up of an alloy of rhodium and platinum dissolved in the solid state is obtained by adding a reductant to a solution containing rhodium ions and platinum ions.

With regard to the metal complex, obtaining a polymer having an infinite number of metal atoms through the use of a polydentate ligand is known. For example, Japanese Patent Application Publication No. JP-A-2000-109485 discloses a technology for obtaining a dicarboxylic acid metal complex polymer having a giant three-dimensional structure through the use of a dicarboxylic acid.

SUMMARY OF THE INVENTION

The invention provides a novel multiple-metal complex-containing compound that allows easy synthesis of large amount of a size-controlled cluster, and a metal complex that can be used for the synthesis of the compound. The invention also provides methods for manufacturing the multiple-metal complex-containing compound and the complex, and methods of using the multiple-metal complex-containing compound and the complex.

A first aspect of the invention relates to a multiple-metal complex-containing compound including two or more metal complexes in each of which a ligand is coordinated to one metal atom or a plurality of metal atoms of the same kind, wherein the two or more metal complexes are bound to each other via a polydentate ligand that substitutes partially the ligands of the two or more metal complexes, and have 2 to 1000 metal atoms.

According to the foregoing aspect, if the ligands are removed from the multiple-metal complex-containing compound by firing or the like, a metal or metal oxide cluster, having the same number of metal atoms as contained in the compound can be obtained.

A second aspect of the invention relates to a manufacture method for a metal or metal oxide cluster that has 2 to 1000 metal atoms, which includes (a) providing a solution containing the multiple-metal complex-containing compound of the invention, and (b) drying and firing the solution.

A third aspect of the invention relates to a manufacture method for a multiple-metal complex-containing compound, which includes: providing a metal complex; providing a polydentate ligand or a polydentate ligand source; and dissolving the metal complex and the polydentate ligand or the polydentate ligand source in a solvent.

According to the foregoing aspect, a multiple-metal complex-containing compound having a controlled number of metal atoms can be obtained by substituting at least only partially the ligands coordinated in the metal complexes, with a polydentate ligand. It is to be noted herein that the term "polydentate ligand source or ligand source" in this specification means a polydentate ligand or a compound (precursor) that provides or a ligand when dissolved in a solvent.

A fourth aspect of the invention relates to a metal complex in which ligands are coordinated to one metal atom or a plurality of metal atoms of the same kind, and at least one of the ligands has an uncoordinated functional group that is not coordinated to a metal atom and that is selected from the group consisting of: —COOH, —COOR$^8$, —CR$^8$R$^9$—OH, —NR$^8${C(=O)R$^9$}, —NR$^8$R$^9$, —CR$^8$=N—R$^9$, —CO—R$^8$, —PR$^8$R$^9$, —P(=O)R$^8$R$^9$, —P(OR$^8$)(OR$^9$), —S(=O)$_2$R$^8$, —S$^+$(—O$^-$)R$^8$, —SR$^8$, —CR$^8$R$^9$—SH, —CR$^8$R$^9$—SR$^{10}$, and —CR$^8$=R$^9$R$^{10}$ (R$^8$ to R$^{10}$ each independently are hydrogen or a monovalent organic group).

According to the foregoing aspect, the characteristics of a functional group that is not coordinated to a metal atom can be utilized. Concretely, through the use of such functional groups, it is possible to stably adsorb the metal complex to a substrate, bind metal complexes to each other, bind the metal complex and another compound, etc.

A fifth aspect of the invention relates to a manufacture method for an exhaust gas purification catalyst, which includes: providing a solution containing the metal complex according to the foregoing aspects; impregnating a catalyst support with the solution; and drying and firing the solution.

According to this aspect, a metal complex is adsorbed to a catalyst support due to the affinity between a functional group not coordinated to a metal atom and the catalyst support, so that when the metal complex is fired or the like, the metal contained in the metal complex can be supported on the catalyst support with high degree of dispersion.

A sixth aspect of the invention relates to a manufacture method for a multiple-metal complex-containing compound, which includes: providing a metal complex that has a ligand that has an uncoordinated carbon-carbon double bond; and dissolving the metal complex in a solvent and substituting an alkylidene group of an uncoordinated carbon-carbon double bond through a cross-metathesis reaction of the carbon-carbon double bond.

According to the foregoing aspect, a multiple-metal complex-containing compound can be manufactured from a metal complex that has an uncoordinated carbon-carbon double bond, through the cross-metathesis reaction of a carbon-carbon double bond (olefin).

BRIEF DESCRIPTION OF THE DRAWINGS

The foregoing and/or further objects, features and advantages of the invention will become more apparent from the following description of preferred embodiment with reference to the accompanying drawings; in which like numerals are used to represent like elements and wherein.

DETAILED DESCRIPTION OF THE PREFERRED EMBODIMENTS

In the following description, the present invention will be described in more detail in terms of exemplary embodiments.

(Multiple-Metal Complex-Containing Compound)

A multiple-metal complex-containing compound in accordance with an embodiment of the invention has a plurality of metal complexes in each of which a ligand incoordinated to one metal atom or a plurality of metal atoms of the same kind. In this compound, a plurality of metal complexes are bound to each other via a polydentate ligand that substitutes partially the ligands, and have 2 to 1000 metal atoms. The number of the metal atoms may be 2 to 100, for example, 2 to 50, or 2 to 20, or 2 to 10.

(Ligand of a Metal Complex)

The ligands of the metal complexes of the multiple-metal complex-containing compound in accordance with the embodiment can be arbitrarily selected, taking into consideration the properties of the multiple-metal complex-containing compound obtained, the steric hindrance between metal complexes to be bound, etc. The ligand may be either a unidentate ligand or a polydentate ligand such as a chelate ligand.

This ligand may be a hydrogen group bound with one functional group selected from the group of functional groups mentioned below, or an organic group bound with one or more functional groups selected from the group of functional groups mentioned below, particularly an organic group bound with one or more functional groups of the same kind selected from the group consisting of: —COO$^-$ (carboxy group), —CR$^1$R$^2$—O$^-$ (alkoxy group), —NR$^{1-}$ (amide group), —NR$^1$R$^2$ (amine group), —CR$^1$=N—R$^2$ (imine group), —CO—R$^1$ (carbonyl group), —PR$^1$R$^2$ (phosphine group), —P(=O)R$^1$R$^2$ (phosphine oxide group), —P(OR$^1$)(OR$^2$) (phosphite group), —S(=)$_2$R$^1$ (sulfone group), —S$^+$(O$^-$)R$^1$ (sulfoxide group), —SR$^1$ (sulfide group), and —CR$^1$R$^2$—S$^-$ (thiolato group); and particularly —COO$^-$ (carboxy group), —CR$^1$R$^2$—O$^-$ (alkoxy group), —NR$^{1-}$ (amide group), and —NR$^1$R$^2$ (amine group) (R$^1$ and R$^2$ each independently are hydrogen or a monovalent organic group).

The organic group bound with a functional group may be a substituted or non-substituted hydrocarbon group, particularly a substituted or non-substituted hydrocarbon group of $C_1$ to $C_{30}$ (i.e., whose carbon atom number is 1 to 30; this will be applied in the following description as well), that may have a hetroatom, an ether bond or an ester bond. In particular, this organic group may be an alkyl group, an alkenyl group, an alkynyl group, an aryl group, an aralkyl group or a monovalent alicyclic group of $C_1$ to $C_{30}$, particularly $C_1$ to $C_{10}$. More particularly, this organic group may be an alkyl group, an alkenyl group, an alkynyl group of $C_1$ to $C_5$, particularly $C_1$ to $C_3$.

$R^1$ and $R^2$ may each independently be hydrogen, or a substituted or non-substituted hydrocarbon group, particularly a substituted or non-substituted hydrocarbon group of $C_1$ to $C_{30}$, that may have a hetroatom, an ether bond or an ester bond. Particularly, $R^1$ and $R^2$ may be hydrogen, or an alkyl group, an alkenyl group, an alkynyl group, an aryl group, an aralkyl group or a monovalent alicyclic group of $C_1$ to $C_{30}$, particularly $C_1$ to $C_{10}$. More particularly, $R^1$ and $R^2$ may be hydrogen, or an alkyl group, an alkenyl group or an alkynyl group of $C_1$ to $C_5$, particularly $C_1$ to $C_3$.

Examples of the ligand of the metal complex include a carboxylic acid ligand (R—COO$^-$), an alkoxy ligand (R—CR$^1$R$^2$—O$^-$), an amide ligand (R—NR$^{1-}$), an amine ligand (R—NR$^1$R$^2$), an imine ligand (R—CR$^1$=N—R$^2$), a carbonyl ligand (R—CO—R$^1$), a phosphine ligand (R—PR$^1$R$^2$), a phosphine oxide ligand (R—P(=O)R$^1$R$^2$), a phosphite ligand (R—P(OR$^1$)(OR$^2$)), a sulfone ligand (R—S(=O)$_2$R$^1$), a sulfoxide ligand (R—S$^+$(O$^-$)R$^1$), a sulfide ligand (R—SR$^1$), and a thiolato ligand (R—CR$^1$R$^2$—S$^-$) (R is hydrogen or an organic group, and R$^1$ and R$^2$ are as mentioned above).

Concrete examples of the carboxylic acid ligand include a formic acid (formato) ligand, an acetic acid (acetato) ligand, a propionic acid (propionato) ligand, and an ethylenediaminetetraacetic acid ligand.

Concrete examples of the alkoxy ligand include a methanol (methoxy) ligand, an ethanol (ethoxy) ligand, a propanol (propoxy) ligand, a butanol (butoxy) ligand, a pentanol (pentoxy) ligand, a dodecanol (dodecyl oxy) ligand, and a phenol (phenoxy) ligand.

Concrete examples of the amide ligand include a dimethyl amide ligand, a diethyl amide ligand, a di-n-propyl amide ligand, a diisopropyl amide ligand, a di-n-butyl amide ligand, a di-t-butyl amide ligand, and a nicotine amide.

Concrete examples of the amine ligand include methyl amine, ethyl amine, methyl ethyl amine, trimethyl amine, triethyl amine, ethylene diamine, tributyl amine, hexamethylene diamine, aniline, ethylene diamine, propylene diamine, trimethylene diamine, diethylene triamine, triethylene tetraamine, tris(2-aminoethypamine, ethanol amine, triethanol amine, ethanol amine, triethanol amine, diethanol amine, trimethylene diamine, piperidine, triethylene tetramine, and triethylene diamine.

Concrete examples of the imine ligand include diimine, ethyleneimine, propyleneimine, hexamethyleneimine, benzophenoneimine, methyl ethyl ketone imine, pyridine, pyrazole, imidazole, and benzoimidazole.

Concrete examples of the carbonyl ligand include carbon monoxide, acetone, benzophenone, acetyl acetone, acenaphthoquinone, hexafluoroacetyl acetone, benzoyl acetone, trifluoroacetyl acetone, and dibenzoyl methane.

Concrete examples of the phosphine ligand include phosphorus hydride, methyl phosphine, dimethyl phosphine, trimethyl phosphine, and diphosphine.

Concrete examples of the phosphine oxide ligand include tributyl phosphine oxide, triphenyl phosphine oxide, and tri-n-octyl phosphine oxide.

Concrete examples of the phosphite ligand include triphenyl phosphite, tritolyl phosphite, tributyl phosphite, and triethyl phosphite.

Concrete examples of the sulfone ligand include hydrogen sulfide, dimethyl sulfone, and dibutyl sulfone.

Concrete examples of the sulfoxide ligand include a dimethyl sulfoxide ligand, and a dibutyl sulfoxide ligand.

Concrete examples of the sulfide ligand include ethyl sulfide, butyl sulfide, etc.

Concrete examples of the thiolato ligand include a methanethiolato ligand, and a benzenethiolato ligand.

(Polydentate Ligand)

As the polydentate ligand that substitutes partially the ligands of a plurality metal complexes and that binds the metal complexes to each other, an arbitrary polydentate ligand that can play the aforementioned role may be used. It is considered preferable that the polydentate ligand have a certain length in order to avoid destabilization of the multiple-metal complex-containing compound due to the steric hindrance between metal complexes. Particularly, in the case where the multiple-metal complex-containing compound in accordance with the embodiment of the invention is subjected to firing or the like so as to obtain a cluster that has the same number of metal atoms as contained in this compound, an excessively great length of the polydentate ligand may possibly make it difficult to obtain a single kind of cluster from the compound.

The polydentate ligand that substitutes partially the Ligands of the metal complexes may be represented by the following formula:

(where R$^3$ is a bond or a bivalent organic group, and L$^1$ and L$^2$ are either the same or different functional groups selected from the group constituting of: —COO$^-$ (carboxy group), —CR$^4$R$^5$—O$^-$ (alkoxy group), —NR$^{4-}$ (amide group), —NR$^4$R$^5$ (amine group), —CR$^4$=N—R$^5$ (imine group), —CO—R$^4$ (carbonyl group), —PR$^4$R$^5$ (phosphine group), —P(=O)R$^4$R$^5$ (phosphine oxide group), —P(OR$^4$)(OR$^5$) (phosphite group), —S(=O)$_2$R$^4$ (sulfone group), —S$^+$(O$^-$)R$^4$ (sulfoxide group), —SR$^4$ (sulfide group), and —CR$^1$R$^4$—S$^-$ (thiolato group) (R$^4$ and R$^5$ each independently are hydrogen or a monovalent organic group)).

In particular, L$^1$ and L$^2$ may represent the same functional group selected from the group consisting of: —COO$^-$ (carboxy group), —CR$^4$R$^5$—O$^-$ (alkoxy group), —NR$^{4-}$ (amide group), and —NR$^4$R$^5$ (amine group) (R$^4$ and R$^5$ each independently are hydrogen or a monovalent organic group).

R$^3$ may be a bond, or a substituted or non-substituted bivalent hydrocarbon group, particularly a substituted or non-substituted bivalent hydrocarbon group of $C_1$ to $C_{30}$, that may have a heteroatom, an ether bond or an ester bond. Particularly, R$^3$ may be an alkylene group, an alkenylene group, an alkynylene group, an arylene group, an aralkylen group or a bivalent alicyclic group of $C_1$ to $C_{30}$ and, particularly $C_1$ to $C_{10}$.

R$^4$ and R$^5$ may be organic groups mentioned in conjunction with R$^1$ and R$^2$.

(Combination of a Polydentate Ligand and a Ligand of a Metal Complex)

The ligands of the metal complexes, and the polydentate ligand substituting partially the ligands of the metal complexes may have the same functional group. For example, the ligands of the metal complexes and the polydentate ligand may each have a carboxy group, an alkoxy group, an amide group, or an amine group.

(Metal That Becomes a Nucleus of a Metal Complex)

The metal that becomes a nucleus of the metal complex may be either a main group metal or a transition metal. This metal may be particularly a transition metal, and more particularly fourth to eleventh group transition metals, for example, a metal selected from the group consisting of titanium, vanadium, chromium, manganese, iron, cobalt, nickel, zirconium, niobium, molybdenum, technetium, ruthenium, rhodium, palladium, silver, hafnium, tantalum, tungsten, rhenium, osmium, iridium, platinum, and gold.

Furthermore, in the case where a catalyst is provided through the use of a multiple-metal complex-containing compound in accordance with the embodiment, the metal to be used may be a metal beneficial for the use of the catalyst, for example, elements of the iron family (iron, cobalt, nickel), copper, platinum group elements (ruthenium, rhodium, palladium, osmium, iridium, and platinum), gold, or silver.

(Metal Complex)

As for the multiple-metal complex-containing compound in accordance with the embodiment, the metal complexes each may be an arbitrary metal complex in which a ligand is coordinated to one metal atom or a plurality of metal atoms of the same kind. That is, the metal complex may be a polynuclear complex, for example, a complex that has 2 to 10 metal atoms, particularly 2 to 5 metal atoms.

This metal complex may be an arbitrary metal complex. Concrete examples of the metal complex include $[Pt_4(CH_3COO)_8]$, $[Pt(acac)_2]$ ("acac" is an acetyl acetonato ligand), $[Pt(CH_3CH_2NH_2)_4]Cl_2$, $[Rh_2(C_6H_5COO)_4]$, $[Rh_2(CH_3COO)_4]$, $[Rh_2(OOCC_6H_4COO)_2]$, $[Pd(acac)_2]$, $[Ni(acac)_2]$, $[Cu(C_{11}H_{23}COO)_2]_2$, $[Cu_2(OOCC_6H_4COO)_2]$, $[Cu_2(OOCC_6H_4CH_3)_4]$, $[Mo_2(OOCC_6H_4COO)_2]$, $[Mo_2(CH_3COO)_4]$, and $[N(n-C_4H_9)_4][Fe^{II}Fe^{III}(ox)_3]$ ("ox" is an oxalic acid ligand).

(Form in Which the Multiple-Metal Complex-Containing Compound Has Carboxylic Acid Ligands)

The multiple-metal complex-containing compound in accordance with the embodiment may be in a form in which the metal complexes are metal complexes that have carboxylic acid ligands, particularly acetic acid ligands, for example, octaacetatotetraplatinum ($[Pt(\mu\text{-}CH_3COO)_8]$), and in which the polydentate ligand substituting partially the ligands of the metal complexes is a dicarboxylic acid ligand.

The dicarboxylic acid ligand may be represented by the following formula:

$$\text{OOC}-R^6-\text{COO}^-$$

($R^6$ is an alkylene group, an alkenylene group, an alkynylene group, an arylene group, an aralkylen group or a bivalent alicyclic group of $C_1$ to $C_{30}$ and, particularly, $C_1$ to $C_{10}$).

$R^6$ may be selected from the group consisting of p-phenylene groups, and alkenylene groups represented by the following formula:

$$-(CH_2)_nC=C(CH_2)_n-$$

(n is an integer of 1 to 5).

(Form in Which the Metal Complexes Are Octaacetatotetraplatinum)

The multiple-metal complex-containing compound in accordance with the embodiment may be represented by the following formula:

$$[Pt_4(CH_3COO)_7(O_2C-R^7-CO_2)(CH_3COO)_7Pt_4]$$

($R^7$ is an alkylene group, an alkenylene group, an alkynylene group, an arylene group, an aralkylen group or a bivalent alicyclic group of $C_1$ to $C_{30}$, particularly $C_1$ to $C_{10}$).

$R^7$ may be selected from the group consisting of p-phenylene groups, and alkenylene groups represented by the following formula:

$$-(CH_2)_nC=C(CH_2)_n-$$

(n is an integer of 1 to 5).

(Manufacture Method for a Metal or Metal Oxide Cluster)

In the manufacture method for a metal or metal oxide cluster having 2 to 1000 metal atoms in accordance with the embodiment, (a) a solution containing the multiple-metal complex-containing compound of the invention is provided, and (b) the solution is dried and fired.

The drying and firing of the solution containing the multiple-metal complex-containing compound can be performed in a condition of a temperature and a time that are sufficient to obtain a metal or metal oxide cluster. For example, the drying may be performed at a temperature of 120 to 250° C. for 1 to 2 hours, and then the firing may be performed at a temperature of 400 to 600° C. for 1 to 3 hours. The solvent of the solution to be used in this method may be an arbitrary solvent that is capable of stably maintaining the multiple-metal complex-containing compound of the invention, for example, an aqueous solvent, or an organic solvent such as dichloroethane, or the like.

This method may further include impregnating a porous support with the solution before drying and firing the solution in the step (b).

In the case where a catalyst, particularly, an exhaust gas purification catalyst, is to be manufactured by using this method, the porous support to be used may be a porous metal oxide support, for example, a porous metal oxide support selected from the group consisting of alumina, ceria, zirconia, silica, titania, and their combinations.

(Manufacture Method for a Multiple-Metal Complex-Containing Compound of the Invention)

In the manufacture method for the multiple-metal complex-containing compound in accordance with the embodiment, (a) a metal complex is provided, and (b) a polydentate ligand or a polydentate ligand source is provided, and (c) the metal complex and the polydentate ligand or the polydentate ligand source are mixed in a solvent.

The polydentate ligand to be used in this method is selected so that the selected polydentate ligand can substitute ligands coordinated in the metal complex for use as a raw material. Therefore, in general, it is possible to use a polydentate ligand that has stronger coordinating power than the ligands coordinated in the metal complex for use as a raw material, particularly a polydentate ligand that has stronger coordinating power than the ligands coordinated in the metal complex for use as a raw material and that has the same number of functional groups as the ligands.

The polydentate ligand may be used in relatively large amount in order to accelerate the substitution of the ligands of the metal complex with the polydentate ligand. However, the amount of the polydentate ligand to be used in this method may be less than the amount that is needed in order to substitute entirely the ligands coordinated in the metal complex. The amount of the polydentate ligand to be used in this method may be ½ or less, or ¼ or less, or ⅛ or less of the amount that is needed in order to substitute entirely the ligands coordinated in the metal complex, from the viewpoint of binding controlled numbers of metal complexes to each other.

The solvent to be used in this method may be an arbitrary solvent capable of stably maintaining the multiple-metal complex-containing compound of the invention, for example, an aqueous solvent, or an organic solvent such as dichloroethane or the like.

(Metal Complex)

The metal complex of the invention is a metal complex in which ligands are coordinated to one metal atom or a plurality of metal atoms of the same kind, and at least one of the ligands has an uncoordinated functional group that is not cooridnated to a metal atom and that is selected from the group consisting of: —COOH (carboxy group), —COOR$^8$ (ester group), —CR$^8$R$^9$—OH (alcohol group), —NR$^8${C(=O)R$^9$} (amide group), —NR$^8$R$^9$ (amine group), —CR$^8$=N—R$^9$ (imine group), —CO—R$^8$ (carbonyl group), —PR$^8$R$^9$ (phosphine group), —P(=O)R$^8$R$^9$ (phosphine oxide group), —P(OR$^8$)(OR$^9$) (phosphite group), —S(=O)$_2$R$^8$ (sulfone group), —S$^{3O}$(—O$^-$)R$^8$ (sulfoxide group), —SR$^8$ (sulfide group), —CR$^8$R$^9$—SH (thiol group), —CR$^8$R$^9$—SR$^{10}$ (thioether group), and —CR$^8$=R$^9$R$^{10}$ (ethylene bond) (R$^8$ to R$^{10}$ each independently are hydrogen or a monovalent organic group).

Independently for each of R$^8$ to R$^{10}$, the organic groups mentioned above in conjunction with R$^1$ and R$^2$ may be cited as examples.

The ligand of the metal complex of the invention may be a hydrogen group bound with a functional group of the following functional groups which is coordinated to a metal atom, or an organic group bound with one or more of the following functional groups which are coordinated to a metal atom: —COO$^-$, —CR$^{11}$R$^{12}$—O$^-$, —NR$^{11-}$, —NR$^{11}$R$^{12}$, —CR$^{11}$=N—R$^{12}$, —CO—R$^{11}$, —PR$^{11}$R$^{12}$, —P(=O)R$^{11}$R$^{12}$, —P(OR$^{11}$)(OR$^{12}$), —S(=O)$_2$R$^{11}$, —S$^+$(—O$^-$)R$^{11}$, —SR$^{11}$, and —CR$^{11}$R$^{12}$—S$^-$ (R$^{11}$ and R$^{12}$ each independently are hydrogen or a monovalent organic group).

Examples the ligand of the metal complex of the invention include the ligands cited above in conjunction with the metal complexes of the multiple-metal complex-containing compound of the invention. Therefore, independently for each of R$^{11}$ and R$^{22}$, the organic groups mentioned above in conjunction with R$^1$ and R$^2$ may be cited as examples.

It is possible that each ligand of the metal complex of the invention have only one functional group coordinated to a metal atom.

(Form in Which the Metal Complex in Accordance with the Embodiment has a Carboxy Group as an Uncoordinated Functional Group)

In the case where the metal complex in accordance with the embodiment has a carboxy group as an uncoordinated functional group, a ligand of the metal complex may have a carboxy group that is coordinated to a metal atom. For example, the metal complex may be in a form in which the ligand having an uncoordinated functional group is a dicarboxylic acid ligand and the ligand not having an uncoordinated functional group is an acetic acid ligand.

Therefore, the metal complex may be an octaacetatotetraplatinum ([Pt(CH$_3$COO)$_8$]) in which at least one acetic acid ligand (acetato ligand) is substituted with a dicarboxylic acid ligand.

The dicarboxylic acid ligand may be represented by the following formula:

OOC—R$^{13}$—COOH

(R$^{13}$ is an alkylene group, an alkenylene group, an alkynylene group, an arylene group, an aralkylen group or a bivalent alicyclic group of C$_1$ to C$_{30}$, particularly C$_1$ to C$_{10}$).

(Form in Which the Metal Complex in Accordance with the Embodiment is Dicarboxylic Acid-Substituted Octaacetatotetraplatinum)

The metal complex may be represented by the following formula:

[Pt$_4$(CH$_3$COO)$_7${O$_2$CR$^{14}$(COOH)}]

(R$^{14}$ is an alkylene group, an alkenylene group, an alkynylene group, an arylene group, an aralkylen group or a bivalent alicyclic group of C$_1$ to C$_{30}$, particularly C$_1$ to C$_{10}$).

R$^{14}$ may be, for example, a p-phenylene group.

(Form in Which the Metal Complex in Accordance with the Embodiment has a Carbon-Carbon Double Bond as an Uncoordinated Functional Group)

In the case where the metal complex in accordance with the embodiment has a carbon-carbon double bond as a uncoordinated functional group, a ligand of the metal complex may have a carboxy group that is coordinated to a metal atom. For example, the metal complex may be in a form in which the ligand having an uncoordinated functional group is a carboxylic acid ligand that has a carbon-carbon double bond, namely, an unsaturated carboxylic acid, and in which the ligand not having an uncoordinated functional group is an acetic acid ligand.

Therefore, the metal complex may be an octaacetatotetraplatinum ([Pt(CH$_3$COO)$_8$]) in which at least one acetic acid ligand is substituted with a carboxylic acid ligand that has a carbon-carbon double bond.

The carboxylic acid ligand having a carbon-carbon double bond may be represented by the following formula:

OOC—R$^{15}$

(R$^{15}$ is an alkenyl group of C$_1$ to C$_{30}$, particularly C$_1$ to C$_{10}$)

(Form in which the Metal Complex in Accordance with the Embodiment is Octaacetatotetraplatinum Substituted with a Carboxylic Acid that has a Carbon-Carbon Double Bond)

The metal complex of the invention may be represented by the following formula:

[Pt$_4$(CH$_3$COO)$_7$(O$_2$CR$^{16}$)]

(R$^{16}$ is a linear chain or branched chain alkenyl group of C$_1$ to C$_{30}$, particularly C$_l$ to C$_{10}$).

(Manufacture Method for an Exhaust Gas Purification Catalyst through the Use of a Metal Complex in Accordance with the Embodiment)

In a manufacture method for an exhaust gas purification catalyst in accordance with the embodiment, (a) a solution containing a metal complex of the invention, particularly a metal complex having, as a nucleus, a metal atom that is preferable for use as a catalyst, is provided, (b) a catalyst support is impregnated with the solution, and (c) the solution is dried and fired.

The catalyst support may be a porous metal oxide support, for example, a porous metal oxide support selected from the group consisting of alumina, ceria, zirconia, silica, titania, and combinations thereof.

The drying and firing of the solution containing the metal complex may be performed in a condition of a temperature and a time that are sufficient to obtain a metal or metal oxide cluster. For example, the drying may be performed at a temperature of 120 to 250° C. for 1 to 2 hours, and then the firing may be performed at a temperature of 400 to 600° C. for 1 to 3 hours. The solvent of the solution to be used in this method may be an arbitrary solvent that is capable of stably maintaining the metal complex of the invention, for example, an aqueous solution, or an organic solution such as dichloroethane or the like.

(Manufacture Method for a Multiple-Metal Complex-Containing Compound through the Use of a Metal Complex in Accordance with the Embodiment that has a Carboxylic Acid Ligand that has a Carbon-Carbon Double Bond)

In a manufacture method for a multiple-metal complex-containing compound through the use of a metal complex in accordance with the embodiment, (a) a metal complex having a carboxylic acid ligand having a carbon-carbon double bond is provided, and (b) the metal complex is dissolved in a solvent, and an alkylidene group of an uncoordinated carbon-carbon double bond is substituted through a cross-metathesis reaction of the carbon-carbon double bond.

The cross-metathesis reaction of the carbon-carbon double bond (olefin) is as follows:

($R^a$ to $R^h$ each independently are an organic group such as a alkyl group or the like).

The cross-metathesis reaction and the catalyst to be used in this reaction are disclosed in, for example, Japanese Patent Application Publication No. JP-A-2004-123925, Japanese Patent Application Publication No. JP-A-2004-043396, and Published Japanese Translation of PCT Application, JP-T-2004-510699. The catalyst for the cross-metathesis reaction may be a fourth-generation Grubbs catalyst. Therefore, the reaction can be caused to progress under mild conditions.

Comparative Example (Synthesis of [$Pt_4(CH_3COO)_8$])

The synthesis of the compound was performed using a procedure described in "Jikken Kagaku Kouza (Experimental Chemistry Course)", 4th ed., Vol. 17, p. 452, Maruzen, 1991. That is, the synthesis was performed as follows. 5 g of $K_2PtCl_4$ was dissolved in 20 ml of warm water, and 150 ml of glacial acetic acid was added to the solution. At this time, $K_2PtCl_4$ began precipitating. Without minding this, 8 g of silver acetate was added. This slurry-like material was refluxed for 3 to 4 hours while being stirred by a stirrer. After the material was let to cool, black precipitation was filtered out. Through the use of a rotary evaporator, acetic acid was removed by concentrating a brown precipitation as much as possible. This concentrate was combined with 50 ml of acetonitrile, and the mixture was left standing. The produced precipitation was filtered out, and the filtrate was concentrated again. Substantially the same operation was performed on the concentrate three times. The final concentrate was combined with 20 ml of dichloromethane, and was subjected to adsorption on a silica gel column. The elution was performed with dichloromethane-acetonitrile (5:1), and a red extract was collected and concentrated to obtain a crystal.

(Supporting)

10 g of magnesium oxide (MgO) was dispersed in 200 g of acetone. While this MgO dispersal solution was being stirred, a solution obtained by dissolving 16.1 mg of [$Pt_4(CH_3COO)_8$] in 100 g of acetone was added. The mixture was stirred for 10 min. When the stirring was stopped, MgO precipitated and a pale red supernatant was obtained (i.e., [$Pt_4(CH_3COO)_8$] did not adsorb to MgO). This mixed solution was concentrated and dried by using a rotary evaporator. The dried powder was fired at 400° C. in air for 1.5 hours. The supported concentration of Pt was 0.1 wt %.

(TEM Observation of Clusters)

Figure 2:
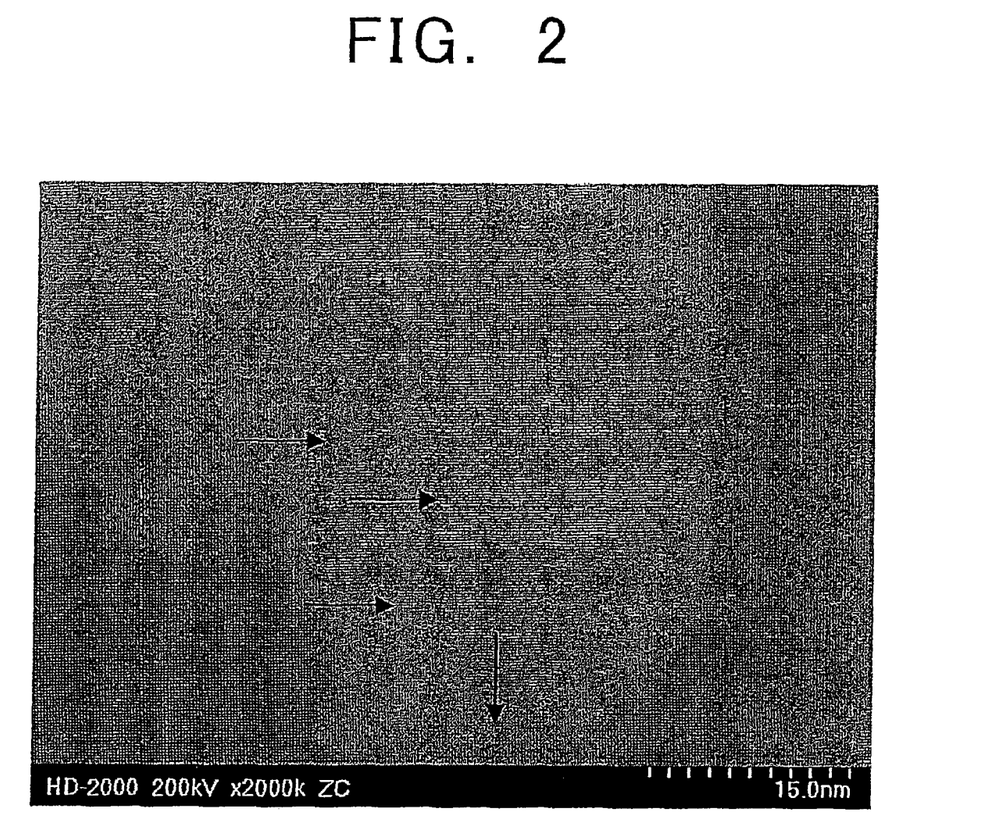
FIG. 2 shows a TEM photograph in which the appearance of Pt on MgO prepared by a method of Comparative Example was observed.

The appearance of the Pt on the MgO prepared by the foregoing method was observed by TEM. Using an HD-2000 type electron microscope of Hitachi, STEM images were observed at an acceleration voltage of 200 kV. An STEM image of Reference Example 1 is shown in FIG. 2. In this image, Pt particles having a spot diameter of 0.6 nm estimated from the structure of 4-platinum atom clusters can be seen, demonstrating that, by the foregoing technique, 4-platinum atom clusters can be supported on an oxide support.

Example 1

(Synthesis of [$Pt_4(CH_3COO)_4$ {o-$C_6H_4$(COO)(COOH)}$_4$])

Figure 3:
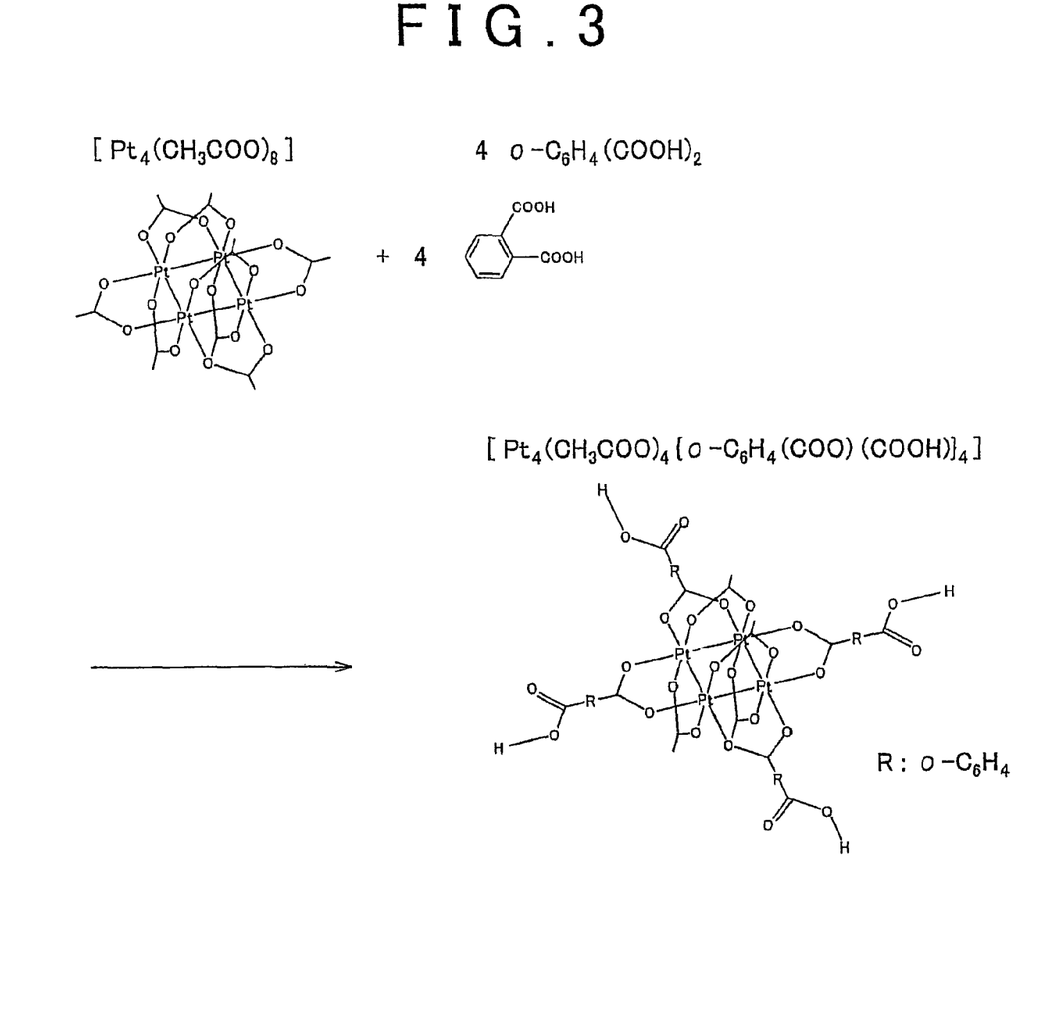
FIG. 3 shows a scheme for synthesizing a compound in accordance with Example 1.

The synthesis of this compound was performed in a scheme shown in FIG. 3.

Concretely, this compound was synthesized as follows. After [$Pt_4(CH_3COO)_8$] (460 mg, 369 μmol) synthesized in the method of Comparative Example and o-$C_6H_4(CO_2H)_2$ (1.50 g, 9.00 mmol) were placed in an argon-substituted Schlenk device of 50 ml, 10 ml of $CH_2Cl_2$ and 10 ml of MeOH were added in that order. Immediately, the solution changed into an orange-red solution. After the solution was stirred at room temperature for 2 hours, the solvent was removed by evaporation under reduced pressure, so that a solid was obtained. This solid was dissolved in $CH_2Cl_2$, and was filtered. The filtrate was dried under reduced pressure to obtain a yellow solid.

The spectral data of the compound, and results of the elementary analysis thereof are shown below.

$^1$H NMR (300 MHz, CDCl$_3$, 308K) δ: 1.96 (s, 12H, CH$_3$), 7.55-7.67 (m, 12H, aromatic H), 8.40-8.43 (m, 4H, aromatic H), 12.3 (br s', $w_{1/2}$=32.4 Hz, 4H, —CO$_2$H).

$^{13}$C{$^1$H} NMR (75 MHz, CDCl$_3$, 308K) δ: 21.3 (O$_2$CCH$_3$), 126.3, 129.1, 129.8, 131.1, 132.1, 135.8 (aromatic C), 176.9 (CO$_2$H), 180.1 (O$_2$CCH$_3$).

IR (KBr disk, ν/cm$^{-1}$): 1715 (C=O), 1557, 1386 (CO$_2^-$).

Anal. Calcd. for $C_{40}H_{32}O_{24}Pt_4$: C, 28.65; H, 1.92. Found: C, 28.63; H, 2.15.

(Structural Confirmation of the Compound)

The structure of the compound was determined through the X-ray structure analysis of the single crystal of the compound obtained in a CH$_2$Cl$_2$ solution.

(Supporting)

10 g of MgO was dispersed in 200g of acetone. While this MgO dispersal solution was being stirred, a solution obtained by dissolving 21.5 mg of [$Pt_4(CH_3COO)_4${o-$C_6H_4$(COO)(COOH)}$_4$] in 100g of acetone was added. This mixture was stirred for 10 min. When the stirring was stopped, MgO precipitated and the supernatant became transparent (i.e., [$Pt_4$($CH_3COO)_4${o-$C_6H_4$(COO)(COOH)}$_4$] adsorbed to MgO). This mixed solution was concentrated and dried by using a rotary evaporator. The dried powder was fired at 400° C. in air for 1.5 hours. The supported concentration of Pt was 0.1 wt %.

(TEM Observation of Clusters)

Figure 4:
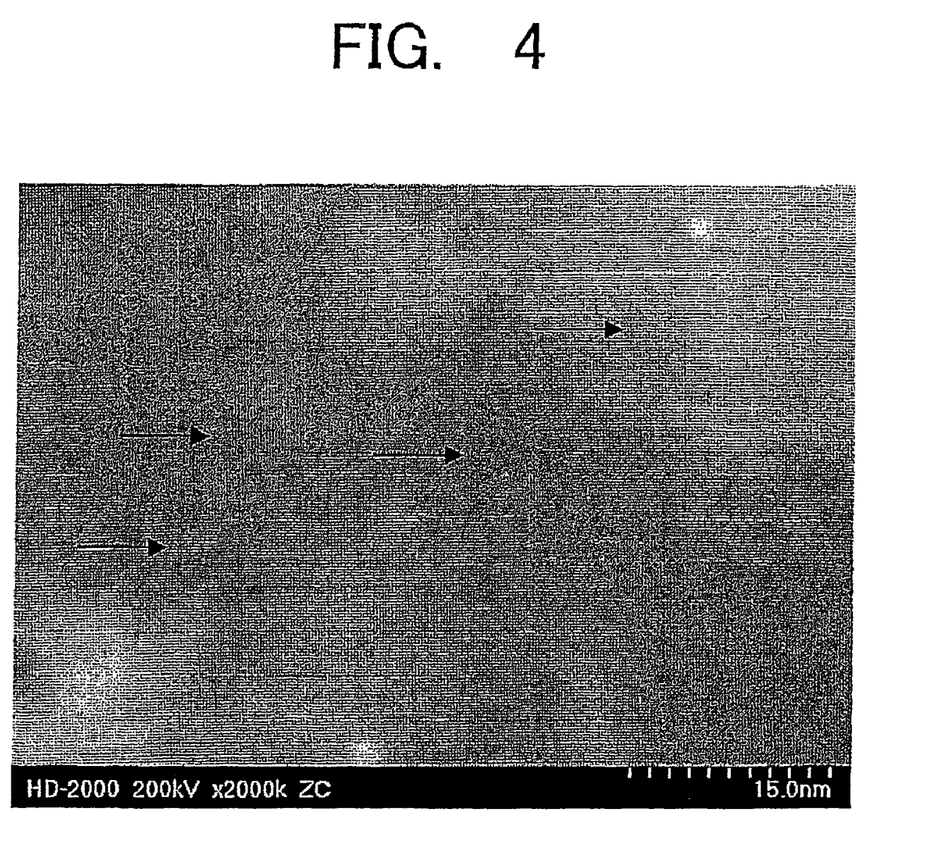
FIG. 4 shows a TEM photograph in which the appearance of Pt on MgO prepared by a method of Example 1 was observed.

The appearance of Pt on MgO prepared in the foregoing method was observed by TEM. Using an HD-2000 type electron microscope of Hitachi, STEM images were observed at an acceleration voltage of 200 kV. An STEM image of Example 1 is shown in FIG. 4. In this image, Pt particles having a spot diameter of 0.6 nm estimated from the structure of 4-platinum atom clusters can be seen, demonstrating that, by the foregoing technique, 4-platinum atom clusters can be supported on an oxide support.

Example 2

(Synthesis of [$Pt_4(CH_3COO)_7${$O_2C(CH_2)_3CH=CH(CH_2)_3CO_2$}($CH_3COO)_7Pt_4$])

Figure 5:
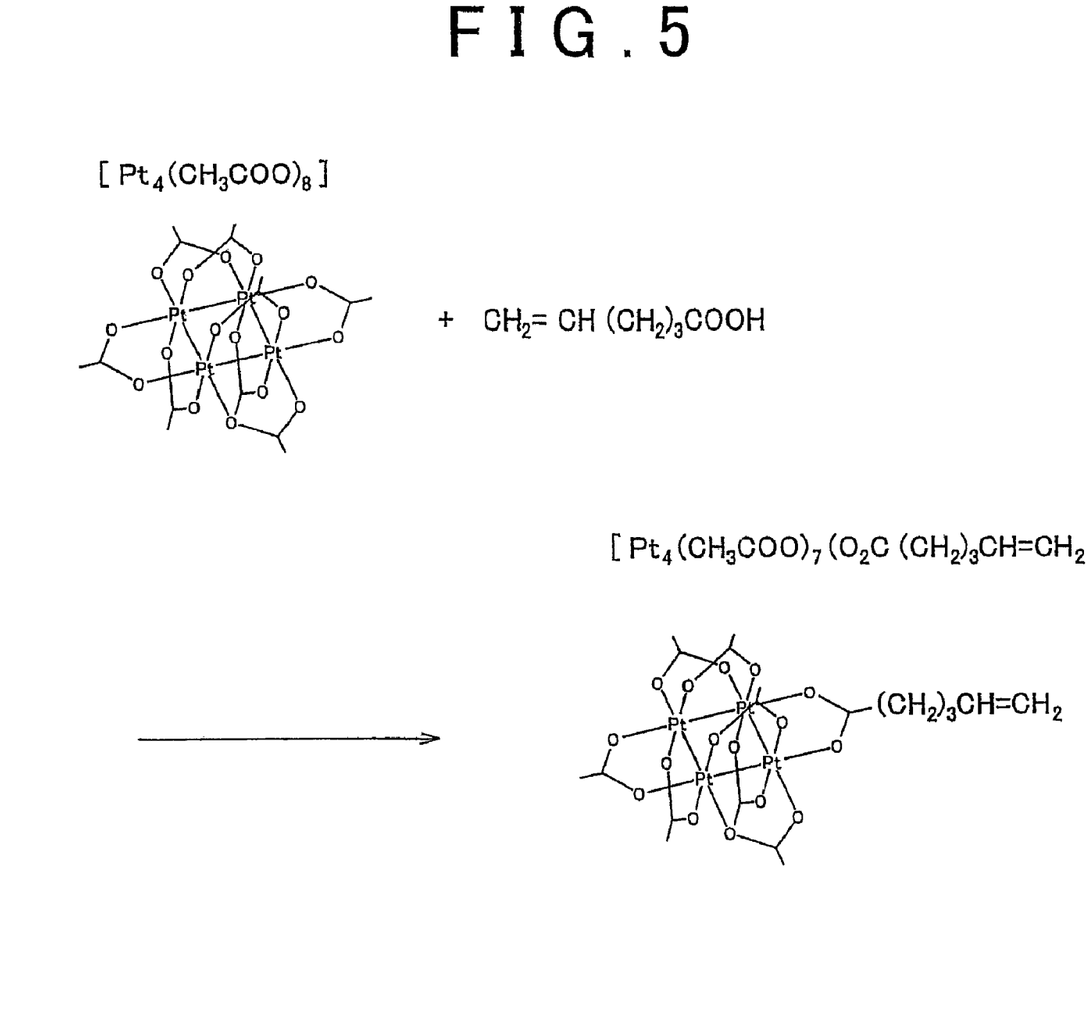
FIG. 5 shows a scheme for synthesizing a compound in accordance with Example 2.
Figure 6:
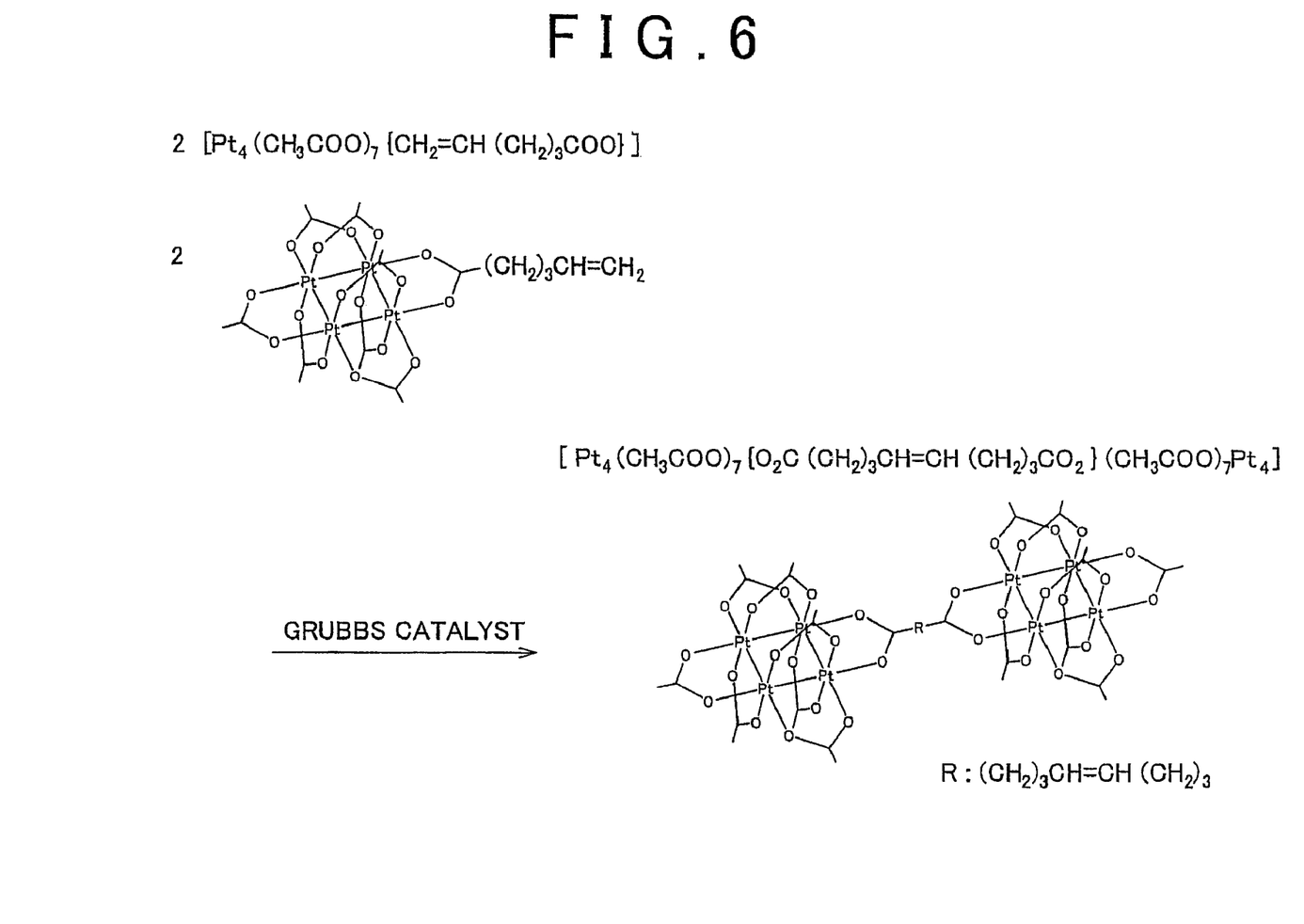
FIG. 6 shows a scheme for synthesizing the compound in accordance with Example 2.

The synthesis of this compound was performed in a scheme shown in FIG. 5 and FIG. 6.

Concretely, this compound was synthesized as follows. $CH_2=CH(CH_2)_3CO_2H$ (19.4 μL, 18.6 mg) was added to a $CH_2Cl_2$ solution (10 mL) of the octaacetatotetraplatinum [$Pt_4(CH_3COO)_8$] (0.204 g, 0.163 mmol) obtained by the procedure shown above in conjunction with Comparative Example 1. This changed the color of the solution from orange to red-orange. After the solution was stirred at room temperature for 2 hours, the solvent was removed by evaporation under reduced pressure, and the remaining substance was washed with diethyl ether (8 mL) twice. As a result, an orange solid of [$Pt_4(CH_3COO)_7${$O_2C(CH_2)_3CH=CH_2$}] was obtained.

[$Pt_4(CH_3COO)_7${$O_2C(CH_2)_3CH=CH_2$}] (362 mg, 0.277 mmol) synthesized as described above and a first-generation Grubbs catalyst (6.7 mg, 8.1 μmol, 2.9 mol %) were placed in an argon-substituted Schlenk device, and were dissolved in $CH_2Cl_2$ (30 mL). A cooling pipe was attached to the Schlenk device, and a heated reflux was performed in an oil bath. After the solution was refluxed for 60 hours, the solvent was removed by evaporation under reduced pressure, and the remaining substance was dissolved in $CH_2Cl_2$. After that, filtration via a glass filter was performed. The filtrate was concentrated under reduced pressure to obtain a solid. The solid was washed with diethyl ether (10 mL) three times to obtain an orange solid of [$Pt_4(CH_3COO)_7${$O_2C(CH_2)_3CH=CH(CH_2)_3CO_2$}($CH_3COO)_7Pt_4$] as an E/Z type mixture.

(Spectral Data)

[$Pt_4(CH_3COO)_7${$O_2C(CH_2)_3CH=CH_2$}]

$^1$H NMR (300 MHz, $CDCl_3$, 308K) δ: 1.89 (tt, $^3J_{HH}$=7.5, 7.5 Hz, 2H, $O_2CCH_2CH_2$—), 1.99 (s, 3H, $^{ax}O_2CCH_3$), 2.00 (s, 3H, $^{ax}O_2CCH_3$), 2.01 (s, 6H, $^{ax}O_2CCH_3$), 2.10 (q like, 2H, —$CH_2CH=CH_2$), 2.44 (s, 6H, $^{eq}O_2CCH_3$), 2.45 (s, 3H, $^{eq}O_2CCH_3$), 2.70 (t, $^3J_{HH}$=7.5 Hz, 2H, $O_2CCH_2CH_2$—), 4.96 (ddt, $^3J_{HH}$=10.4 Hz, $^2J_{HH}$=1.8 Hz, $^4J_{HH}$=? Hz, 1H, —CH=C(H)$^{cis}$H), 5.01 (ddt, $^3J_{HH}$=17.3 Hz, $^2J_{HH}$=1.8 Hz, $^4J_{HH}$=? Hz, 1H, —CH=C(H)$^{trans}$H), 5.81 (ddt, $^3J_{HH}$=17.3, 10.4, 6.6 Hz, 1H, —CH=$CH_2$).

$^{13}C${$^1$H} NMR (75 MHz, $CDCl_3$, 308K) δ: 21.2, 21.2 ($^{ax}O_2CCH_3$), 22.0, 22.0 ($^{eq}O_2CCH_3$), 25.8 ($O_2CCH_2CH_2$—), 33.3 (—$CH_2CH=CH_2$), 35.5 ($O_2CCH_2CH_2$—), 115.0 (—CH=$CH_2$), 137.9 (—CH=$CH_2$), 187.5, 193.0, 193.1 ($O_2CCH_3$), 189.9 ($O_2CCH_2CH_2$—).

MS (ESI+, $CH_3CN$ solution) m/z: 1347 ([M+sol.]$^+$).

IR (KBr disk, v/cm$^{-1}$): 2931, 2855 ($v_{C-H}$), 1562, 1411 ($v_{COO-}$), 1039, 917 ($v_{-C=C-}$).

(Spectral Data)

[$Pt_4(CH_3COO)_7${$O_2C(CH_2)_3CH=CH(CH_2)_3CO_2$}($CH_3COO)_7Pt_4$]

Major(E type):

$^1$H NMR (300 MHz, $CDCl_3$, 308K) δ: 1.83 (like, J=7.7 Hz, 4H, $O_2CCH_2CH_2$—), 2.00 (s, 6H, $^{ax}O_2CCH_3$), 2.01 (s, 18H, $^{ax}O_2CCH_3$), 2.02-2.10 (m, 4H, —$CH_2CH=CH$—), 2.44 (s, 18H, $^{eq}O_2CCH_3$), 2.67 (t, $^3J_{H-H}$=7.2 Hz, 4H, $O_2CCH_2CH_2$—), 5.37-5.45 (m, 2H, —CH=).

$^{13}$C NMR (75 MHz, $CDCl_3$, 308K) δ: 21.1$_7$ (q, $^1J_{C-H}$=130.9 Hz, $^{ax}O_2CCH_3$), 21.2$_2$ (q, $^1J_{C-H}$=131.1 Hz, $^{ax}O_2CCH_3$), 21.9 (q, $^1J_{C-H}$=129.4 Hz, $^{eq}O_2CCH_3$), 22.0 (q, $^1J_{C-H}$=129.4 Hz, $^{eq}O_2CCH_3$), 26.4 (t, $^1J_{C-H}$=127.3 Hz, $O_2CCH_2CH_2$—), 32. (t, $^1J_{C-H}$=127.3 Hz, —$CH_2CH=CH$—), 35.5 (t, $^1J_{C-H}$=130.2 Hz, $O_2CCH_2CH_2$—), 130.1 (d, $^1H_{C-H}$=148.6 Hz, —CH=), 187.3, 187.4, 193.0 ($O_2CCH_3$), 189.9 ($O_2CCH_2CH_2$—).

Minor (Z type):

$^1$H NMR (300 MHz, $CDCl_3$, 308K) δ: 1.83 (like, J=7.7 Hz, 4H, $O_2CCH_2CH_2$—), 2.00 (s, 6H, $^{ax}O_2CCH_3$), 2.01 (s, 18H, $^{ax}O_2CCH_3$), 2.02-2.10 (m, 4H, —$CH_2CH=CH$—), 2.44 (s, 18H, $^{eq}O_2CCH_3$), 2.69 (t, $^3J_{H-H}$=7.2 Hz, 4H, $O_2CCH_2CH_2$—), 5.37-5.45 (m, 2H, —CH=).

$^{13}$C NMR (75 MHz, $CDCl_3$, 308K) δ: 21.1$_7$ (q, $^1J_{C-H}$=130.9 Hz, $^{ax}O_2CCH_3$), 21.2$_2$ (q, $^1J_{C-H}$=131.1 Hz, $^{ax}O_2CCH_3$), 21.9 (q, $^1J_{C-H}$=129.4 Hz, $^{eq}O_2CCH_3$), 22.0 (q, $^1J_{C-H}$=129.4 Hz, $^{eq}O_2CCH_3$), 26.5 (t, $^1J_{C-H}$=127.3 Hz, $O_2CCH_2CH_2$—), 26.7 (t, $^1J_{C-H}$=127;3 Hz, —$CH_2CH=CH$—), 35.5 (t, $^1J_{C-H}$=130.2 Hz, $O_2CCH_2CH_2$—), 129.5 (d, $^1J_{C-H}$=154.3 Hz, —CH=), 187.3, 187.4, 193.0 ($O_2CCH_3$), 189.9 ($O_2CCH_2CH_2$—).

MS (ESI+, $CH_3CN$ solution) m/z: 2584 ([M]$^+$).

(Supporting)

10 g of MgO was dispersed in 200 g of acetone. While this MgO dispersal solution was being stirred, a solution obtained by dissolving 16.6 mg of [$Pt_4$(CH COO)$_7${$O_2C(CH_2)_3CH=CH(CH_2)_3CO_2$}—($CH_3COO)_7Pt_4$] in 100 g of acetone was added. The mixture was stirred for 10 min. This mixed solution was concentrated and dried by using a rotary evaporator. The dried powder was fired at 400° C. in air for 1.5 hours. The supported concentration of Pt was 0.1 wt %.

(TEM Observation of Clusters)

Figure 7:
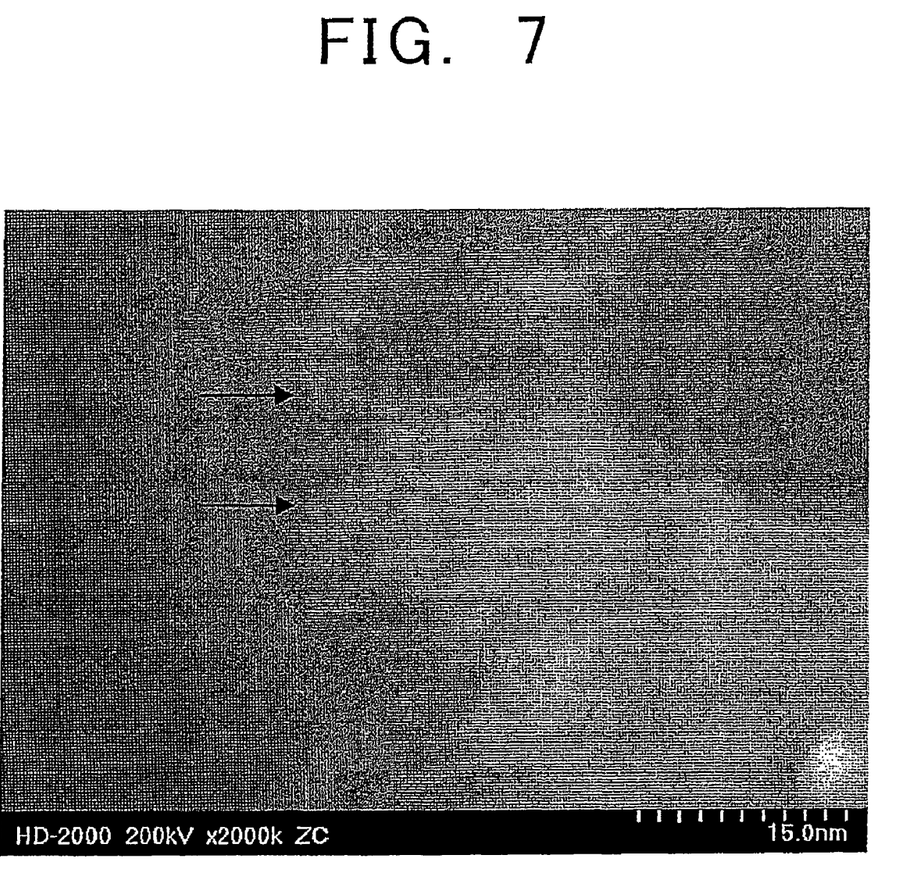
FIG. 7 shows a TEM photograph in which the appearance of Pt on MgO prepared by a method of Example 2 was observed.

The appearance of the Pt on the MgO prepared by the foregoing method was observed by TEM. Using an HD-2000 type electron microscope of Hitachi, STEM images were observed at an acceleration voltage of 200 kV. An STEM image of Example 2 is shown in FIG. 7. In this image, Pt particles having a spot diameter of 0.9 nm estimated from the structure of 8-platinum atom clusters can be seen, demonstrating that, by the foregoing technique, 8-platinum atom clusters can be supported on an oxide support.

Example 3

(Synthesis of [$Pt_4(CH_3COO)_7${$O_2C$-(p-$C_6H_4$)—$CO_2$}($CH_3COO)_7Pt_4$])

Figure 8:
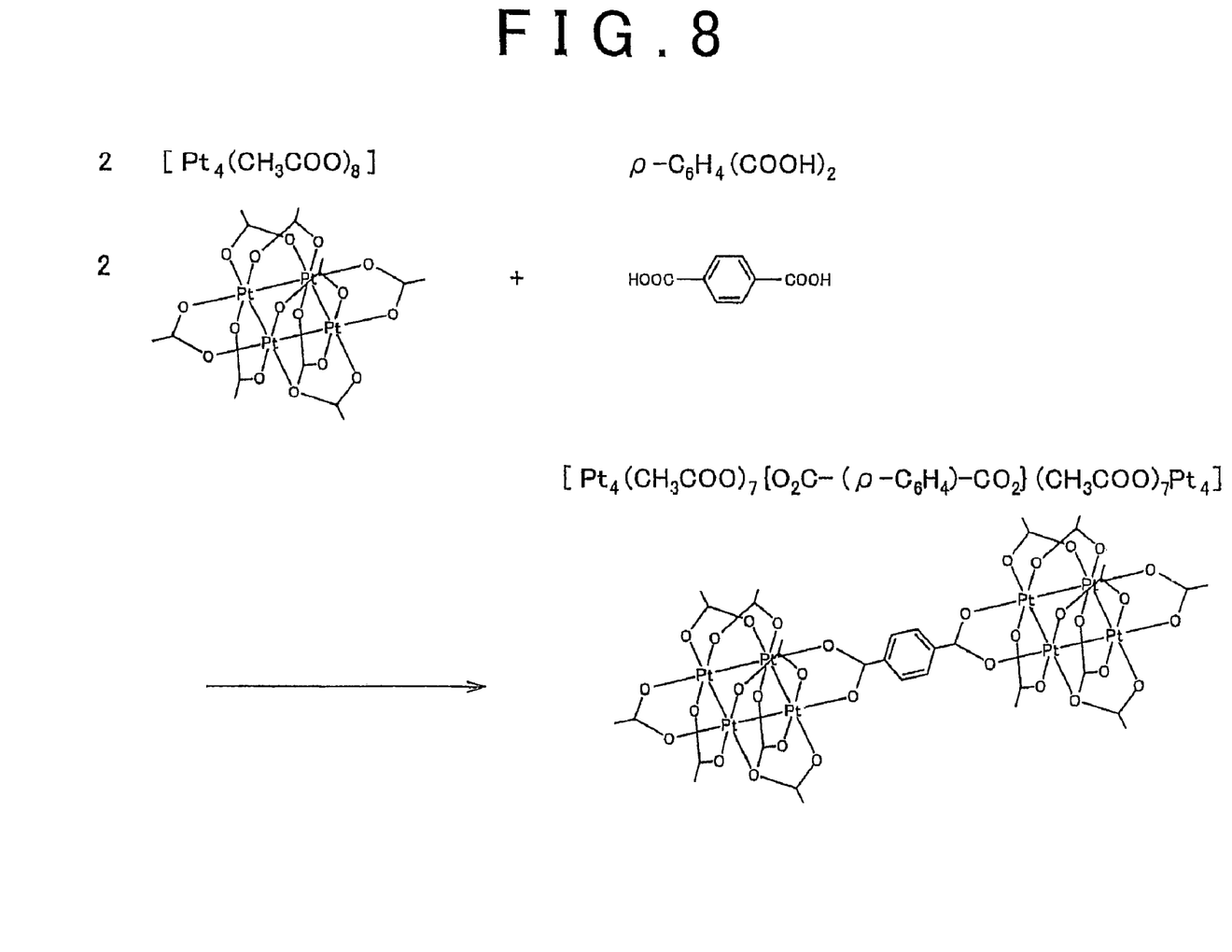
FIG. 8 shows a scheme for synthesizing a compound in accordance with Example 3.

The synthesis of this compound was performed in a scheme shown in FIG. 8.

Concretely, this compound was synthesized as follows. A $CH_2Cl_2$ solution (10 mL) of $[Pt_4(CH_3COO)_8]$ (0.204g, 0.163 mmol) obtained by substantially the same procedure as in Comparative Example was combined with an amount of terephthalic acid ($HO_2C$-(p-$C_6H_4$)—$CO_2H$) (0.0135g, 0.0815 mmol) that was half the amount of $[Pt_4(CH_3COO)_8]$. As a result, a black precipitation was produced. This precipitation was washed twice with $CH_2Cl_2$ (10 mL) to obtain crystal of $[Pt_4(CH_3COO)_7\{O_2C\text{-}(p\text{-}C_6H_4)\text{—}CO_2\}(CH_3COO)_7Pt_4]$.

(Identification)

The compound was identified by elementary analysis since the crystal of the compound did not dissolve in solvents. Results were as shown below.

Anal. Calcd. for $C_{36}H_{46}O_{32}Pt_8$: C, 16.95; H, 1.82. Found: C, 20.10; H, 1.78.

While the invention has been described with reference to exemplary embodiments thereof, it should be understood that the invention is not limited to the exemplary embodiments or constructions. To the contrary, the invention is intended to cover various modifications and equivalent arrangements. In addition, while the various elements of the exemplary embodiments are shown in various combinations and configurations, which are exemplary, other combinations and configurations, including more, less or only a single element, are also within the spirit and scope of the invention.

The invention claimed is:

1. A multiple-metal complex-containing compound, which has 2 to 1000 metal atoms and which comprises a plurality of metal complexes in each of which a carboxylic acid ligand is coordinated to one metal atom or a plurality of metal atoms of the same kind, wherein the plurality of metal complexes are bound to each other by a dicarboxylic acid ligand that substitutes partially the carboxylic acid ligands of the plurality of transition metal complexes, and wherein the transition metal complexes each are octaacetatotetraplatinum.

2. A multiple-metal complex-containing compound, which has 2 to 1000 metal atoms and which comprises a plurality of metal complexes in each of which a carboxylic acid ligand is coordinated to one metal atom or a plurality of metal atoms of the same kind, wherein the plurality of metal complexes are bound to each other by a dicarboxylic acid ligand that substitutes partially the carboxylic acid ligands of the plurality of transition metal complexes, and wherein said wherein said compound is represented by a formula below:

($R^7$ is an alkylene group, an alkenylene group, an alkynylene group, an arylene group, an aralkylene group or a bivalent alicyclic group of $C_1$ to $C_{30}$).

* * * * *